United States Patent
Metzner et al.

(10) Patent No.: US 6,447,774 B1
(45) Date of Patent: Sep. 10, 2002

(54) STABILIZED PROTEIN PREPARATIONS FOR A TISSUE ADHESIVE

(75) Inventors: Hubert Metzner; Peter Gronski, both of Marburg (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 09/856,195

(22) PCT Filed: Nov. 16, 1999

(86) PCT No.: PCT/EP99/08812

§ 371 (c)(1),
(2), (4) Date: Jul. 13, 2001

(87) PCT Pub. No.: WO00/29041

PCT Pub. Date: May 25, 2000

(30) Foreign Application Priority Data

Nov. 18, 1998 (DE) .......................................... 198 53 033

(51) Int. Cl.⁷ ........................ A61K 38/48; A61K 38/00; A61K 35/14; C07K 17/00
(52) U.S. Cl. ........................ 424/94.64; 424/529; 514/2; 530/381; 530/382; 530/383
(58) Field of Search .............................. 424/94.64, 529; 514/21, 2; 530/381, 382, 383

(56) References Cited

U.S. PATENT DOCUMENTS

| | | | |
|---|---|---|---|
| 4,427,651 A | | 1/1984 | Stroetmann |
| 4,453,939 A | | 6/1984 | Zimmerman et al. |
| 5,330,974 A | | 7/1994 | Pines et al. |
| 5,525,648 A | * | 6/1996 | Ansen et al. |
| 5,605,887 A | * | 2/1997 | Pines et al. |
| 5,795,571 A | | 8/1998 | Cederholm-Williams et al. |
| 5,804,428 A | * | 9/1998 | Edwardson et al. |
| 5,962,405 A | | 10/1999 | Seelich |
| 6,084,074 A | * | 7/2000 | Kato et al. |
| 6,096,309 A | * | 8/2000 | Prior et al. |

FOREIGN PATENT DOCUMENTS

| | | | |
|---|---|---|---|
| DE | A-10012732 | | 9/2001 |
| DK | 1493614 | * | 6/1965 |
| EP | 0 554 570 A2 | | 8/1993 |
| EP | 0 804 933 A2 | | 11/1997 |
| WO | WO 92/22312 | | 12/1992 |
| WO | WO 94/00566 | | 1/1994 |
| WO | WO 96/22115 | | 7/1996 |
| WO | WO 97/28832 | | 8/1997 |

OTHER PUBLICATIONS

Chabbat, J., et al., "Properties of a New Fibrin Glue Stable in Liquid State," *Thrombosis Research*, 76(6):525–533 (1994).

De Iaco, PierAndrea, et al., "Fibrin Sealant in Laparoscopic Adhesion Prevention in the Rabbit Uterine Horn Model," *Fertility and Sterility* 62(2):400–404 (1994).

Evrard, V.A.C., et al., "Peritoneal Healing After Fibrin Glue Application: A Comparative Study in a Rat Model," *Human Reproduction* 11(9):1877–1880 (1996).

Gauwerky, J.F.H., et al., "The Effect of Fibrin Glue and Peritoneal Grafts in the Prevention of Intraperitoneal Adhesions," *Arch. Gynecol. Obstet.* 247:161–166 (1990).

Lindenberg, S., et al., "Prevention of Peritoneal Adhesion Formation by Fibrin Sealant," *Annales Chirurgiae et Gynaecologiae* 73:11–13 (1984).

Moro, Hisanaga, et al., "The Effect of Fibrin Glue on Inhibition of Pericardial Adhesions," *The Japanese Journal of Thoracic and Cardiovascular Surgery* 47(2):79–84 (1999).

Takeuchi, Hiroyuki et al., "Effects of Fibrin Glue on Post-surgical Adhesions After Uterine or Ovarian Surgery in Rabbits," *J. Obstet. Gynaecol. Res.* 23(5):479–484 (1997).

English Translation of German Patent Application No. DE–A–10012732.

Abstract for EP 0 554 570 A2, Hock et al., "Stable fibrinogen solution", esp@net database.

* cited by examiner

*Primary Examiner*—Christopher R. Tate
*Assistant Examiner*—Randall Winston
(74) *Attorney, Agent, or Firm*—Finnegan, Henderson, Farabow, Garrett & Dunner, LLP

(57) ABSTRACT

A tissue adhesive is described, which contains three separate components, i.e.,

- a stabilized, essentially fibrinogen-free protein preparation that is of storage-quality in liquid state and contains the blood coagulation factor XIII
- a stabilized protein preparation that is of storage-quality in liquid state and contains fibrinogen. A chaotropic substance of less than 0.28 mol/liter was added to said protein preparation to avoid or reduce the aggregation of fibrinogen, and
- a preparation containing thrombin, which are provided in one packaging unit prepared to be used together.

Furthermore, stabilized, frozen or lyophilized protein preparations containing fibrinogen and Factor XIII are described. Said protein preparations contain fibrinogen- and Factor XIII which remains stable for more than four weeks after defrosting or reconstitution, as well as one or more added chaotropic substances in a quantity of less than 0.28 mol/liter which prevents or reduces the aggregation of fibrinogen and contain inorganic salts of <100 mmol/liter, preferably <50 mmol/liter.

20 Claims, No Drawings

STABILIZED PROTEIN PREPARATIONS FOR A TISSUE ADHESIVE

The subject matter of the invention is a tissue adhesive as well as stabilized protein preparations for a tissue adhesive or preparations for parenteral application, which have no significant loss of effect after being stored in a liquid state or after being defrosted following storage in a frozen state and during further storage in a liquid state over a period of several months or years.

It is already known that tissue adhesives can be used to connect human or animal tissue, and that the main components of such tissue adhesives include fibrinogen, Factor XIII and thrombin. These protein preparations require careful stabilization to retain their full effect and their application properties until they are used for gluing tissue during surgery.

Tissue gluing is a method that has already been described at the turn of the century and repeatedly thereafter (S. Bergel: On the effects of fibrin. *Dt. med. Wschr.* 35:663–5 (1909); E. P. Cronkite, E. L. Lozner, J. M. Deaver: Use of thrombin and fibrinogen in skin grafting. JAMA 124:976–8 (1944); H. Matras; H. P. Dinges, H. Lassmann, B. Mammoli, *Wr. Med. Wschr.* 37:517 (1972); H. Matras, H. P. Dinges, H. Lassmann, B. Mammoli: *J. max. fac. Surg.* 1:37 (1973); H. Matras, F. Braun, H. Lassmann, H. P. Ammrer, B. Mammoli: Plasma clot welding of nerves (experimental report), *J. max. fac. Surg.* 1:2364 (1973); H. Kudema, H. Matras, *Wiener klin. Wschr.* 87:495–496 (1975). Initially, plasma or fibrinogen was still used as powder; later on, purified fibrinogen was used, for example, in the form of a cryoprecipitate.

With the commercial production of fibrinogen-/Factor XIII- and thrombin concentrates since the Seventies, the importance of tissue gluing has increased significantly. It is now used, for example, to support sutures, local haemostasis, the sealing of body cavities to avoid loss of fluid, and for wound care. Tissue gluing with fibrin adhesives is a physiological method and therefore has advantages compared to the synthetic adhesives with respect to compatibility and biodegradability of the adhesive components.

Tissue adhesives are commercially available either as lyophilizates or as frozen preparations. However, after reconstitution or after defrosting, the products are stable in solution for only a few days, because with the highly concentrated fibrinogen-/Factor XIII-solutions, an aggregation and therefore an (for example, proteolytic) inactivation occurs, which makes any further use impossible.

The tissue adhesives that have been described in the literature until now are not yet commercially available and are generally comprised of frozen or freeze-dried components that must be defrosted or dissolved prior to use. To improve the processing, the solubility, the defrosting or the stability of the fibrinogen concentrate, European patent 0,085,923, German patent application 196,17,369 and European patent application 0,856,317 describe the use of chaotropic agents or additives such as arginine or urea or their derivatives or derivatives of benzene, imidazole, pyrozol, furan, thiazole and purine, which generally improve the solubility of proteins. Chaotropic agents in this context are agents that reduce or destabilize the reciprocal effect between proteins or parts thereof and therefore reduce their tendency towards aggregation. It is important to guarantee the stability of the components such as fibrinogen and Factor XIII even in the presence of said chaotropic agents and under the selected conditions. So far, this has not been successful with frozen fibrinogen-/Factor XIII-concentrations that had to be stored for several weeks or months in liquid form after defrosting, or with fibrinogen-/Factor XIII-concentrations that could be stored only in liquid form.

With liquid storage, but especially also with storage in frozen state, the loss of F XIII-activity in the formulations described thus far was so high that in the presence of effective quantities of chaotropic agents, the F XIII-content often clearly drops after only a few weeks or months, often even below the detection limit.

With the formulations in accordance with European patent application 0,856,317, it was shown that tranexaminic acid (AMCA), especially in the presence of chaotropic agents such as arginine and inorganic salts, clearly reduced the F XIII content in the course of storage at −20° (Table 1 b, Batch 1). Storage at 4° Celsius leads to an increase in viscosity in this formulation (Table 1 a, Batch 1), which also rules out a long-term term storage. Thus, these formulations must be considered non-stable in view of the simultaneous stability of fibrinogen and F XIII. Formulations in accordance with DE 196,17,369 also indicate problems in maintaining F XIII-activity (see Table 1, Batch 2 and 2).

Another biological adhesive for human or animal tissue is known from the European patent specification 0,487,713. Said adhesive is stabilized in liquid form at low temperatures. This is supposed to be achieved in that the preparation containing fibrinogen comprises at least one chaotropic agent in a concentration between approximately 0.3 M and 1 M and in that the adhesive is liquid at the storage temperature.

Such fibrinogen concentrate typically comprised about 4 mmol tri-sodium citrate, 240 mmol NaCl, 80 mmol—amino caproic acid (EACA), 240 mmol glycine, 1% polysorbate, 0.6 grams/liter sodium caprolate, 0.5 mol urea, 2,000 KIE/ml aprotinin, if necessary, and a pH of 7.5. The stability was evaluated after only one month, which is very short for a therapeutic preparation. The F XIII-activity was not analyzed. J. Chabbat et al. reported about a fibrinogen concentrate that remains stable in liquid state at 4° Celsius over a period of six months (J. Chabbat, M. Tellier, P. Porte and M. Steinbuch: Properties of a new fibrin glue stable in liquid state. Thromb. Res. 76: 525–533 (1994)). In addition to other formulation components, typically 60 mmol/liter NaCl, 20 mmol/liter EACA and 60 mmol/liter glycine, this concentration comprised 0.5 mol urea or 5% arginine (=0.29 mol). However, the F XIII-strength of this concentration was also not tested.

These liquid formulations, which were described in the European patent specification 0,487,713 and in the literature, are characterized in that the aggregation (polymerization) and thus the increase in viscosity of the concentrated fibrinogen component, is prevented or reduced at refrigeration temperatures. However, Factor XIII, an essential component of fibrinogen concentrates for fibrin glues, is inactivated to a greater or lesser degree under these conditions. In the formulations provided for storage in cooled state in accordance with European patent specification 0,487,713 or the related publication by Chabbat et al. (J. Chabbat, M. Tellier, P. Porte and M. Steinbuch: Properties of a new fibrin glue stable in liquid state. Thromb. Res. 76:525–533 (1994)), the instability of F XIII is therefore a significant problem that is not solved by the proposed formulations (see Table 1, Batches 4–5). Furthermore, the strength of chaotropic agents is relatively high at 0.3 to 1.0 mol/liter, which makes lesser concentrations of chaotropic agents appear desirable (<0.3 mol/liter).

Thus, it can be noted that it was found in the analysis of the stability of fibrinogen/Factor XIII preparations as well as the viscosity of various known fibrinogen/Factor XIII-preparations in refrigerated state (0 to 10° Celsius) or frozen state with subsequent storage in refrigerated state (0 to 10° Celsius) that the previously described formulations do not lead to stable protein preparations. Either the fibrinogen or Factor XIII show a significant reduction in activity during the storage time, or the aggregation of fibrinogen leads to a viscous material that can no longer be applied (see Table 1, Batches 1 to 5).

Thus, the problem to be solved was to develop protein preparations that are liquid and stable over several months, or frozen and stable over several months following defrosting, in which the fibrinogen and/or Factor XIII are stabilized over months or years without any significant loss of effect.

The problem is solved with stabilized protein preparations that in comparison to the state of the art have the advantage that in a first embodiment not only fibrinogen but also Factor XIII is stabilized by the additives and that the content of chaotropic reactants can be reduced, or that in a second embodiment fibrinogen and Factor XIII are formulated separately and thus remain stable.

This is achieved in that for frozen preparations and preparations that must be kept stable for several weeks or months following defrosting, a chaotropic agent corresponding to the definition provided here is used in a lower concentration to avoid the aggregation of fibrinogen, and that the concentration of inorganic salts is reduced and that, if necessary, an antifibrinolytic as well as other common additives and buffer substances are used. A fibrinogen preparation used for this purpose can also contain Factor XIII from the starter material as well as other plasma proteins, such as fibronectin and von Willebrand-Factor (vWF), or it can contain purified Factor XIII as an additive.

Aprotinin or lysine or e-amino caproic acid (EACA) or p-aminomethylbenzoic acid (PAMBA) or their physiologically safe salts can be used as an antifibrinolytic. Studies on the influence of various antifibrinolytics have surprisingly shown that lysine, PAMBA or EACA do not have a negative effect on the activity of F XIII, while tranexaminic acid does. Especially with frozen fibrinogen/F XIII mixtures, but also with fibrinogen/F XIII mixtures stored in liquid state, the use of EACA or lysine is therefore preferred to the use of AMCA. Other stabilizers can be used for F XIII, such as sodium citrate, amino acids and sugar.

Instead of the aforementioned protein preparations, which comprise Factor XIII as well as fibrinogen and their respective stabilizers, it is also possible, and for reasons of better stability even preferable, to store both concentrations separately and only mix them with the thrombin-containing preparation immediately prior to using them as tissue adhesive. The subject matter of the invention is therefore also a tissue adhesive that is comprised of a solution that contains the stabilized factor XIII, a solution that contains the stabilized fibrinogen, and a solution that contains stabilized thrombin, which are provided separately in one packaging unit prepared to be used together. Another advantage of this is that the ratio of Factor XIII and fibrinogen can be changed and adapted to the specific situation as needed.

A) Frozen or lyophilized concentrates that can be stored in liquid state for several weeks/months at 0 to 10° Celsius (see Table 1)

Stable, frozen fibrinogen concentrates are known and have been described, but their stability after defrosting is limited to a few days. The limited stability of the fibrinogen concentrate is, among other things, also attributable to the fact that the viscosity soon increases due to the aggregation of the fibrinogen. It is possible to obtain a low viscosity in the liquid state by adding compounds that prevent aggregation, i.e., chaotropic compounds, but these agents have the disadvantage that they lead to a drop in the Factor XIII-activity in frozen state (for example, at −20° Celsius). Generally, the loss of F XIII-activity occurs in proportion to the concentration of chaotropic agents, i.e., the higher the concentration of chaotropic agents, the quicker the loss of F XIII-activity.

In the development of the stabilized protein preparations in accordance with the invention, it was now found that not all chaotropic agents have the same influence on the stability of the Factor XIII, and that the other additives to be added in accordance with the invention also have a significant influence on the Factor XIII stability and on the viscosity affected by the fibrinogen aggregation. For example, at the same molarity, arginine is significantly more effective in the prevention of fibrinogen polymerization or aggregation than urea. Furthermore, anti-fibrinolytic additives such as the ε-amino caproic acid (EACA), p-aminomethylcyclohexanecarboxylic acid (AMCA) or p-aminomethylbenzoic acid (PAMBA) as well as their physiologically safe salts have an effect on fibrinogen aggregation and F XIII stability. AMCA, especially, has a negative effect on F XIII-activity at storage in frozen state. Surprisingly, EACA, which has a chemical structure very similar to that of AMCA, does not cause the same Factor XIII-drop as AMCA under appropriate conditions. It was further found that F XIII-activity in frozen protein concentrates is not reduced in the presence of specific concentrations of chaotropic agents when the addition of inorganic salts, which until now was common in preparations of this type, is completely abandoned or limited as much as possible. Thus, in the preparation developed in accordance with the invention, fibrinogen and Factor XIII remain liquid and the activity is maintained for at least several weeks or even months after freezing and defrosting, if said formulation comprises a chaotropic compound in a quantity of less than 0.28 mol/liter of a substance that avoids or reduces the aggregation of fibrinogen. Arginine in a quantity of approximately 2 percent by weight has proven especially advantageous. Other slightly chaotropic agents such as citrulline, nicotine amide, urea, etc. or mixtures thereof, for example with arginine, can be used in a quantity of up to 0.28 M, especially of 0.1 to 0.20 M. Furthermore, it is also possible to add water-soluble inorganic salts in concentrations of $\leq$100 mmol/liter, especially $\leq$50 mmol/liter, and in particular, preferably in concentrations of $\leq$20 mmol/liter in addition to the anti-fibrinolytic compound.

In one of the preparations in accordance with the invention, the fibrinogen as well as Factor XIII remain stable for at least several weeks or months during storage in frozen as well as in liquid state. The addition of other components, such as salts of citric acid or lactic acid or one or several amino acids or a mono- or disaccharide or a sugar alcohol or one of their mixtures can also favorably influence the stability. With these compositions, the preparation in accordance with the invention can be refrozen and defrosted or refrozen after reconstitution of a fibrin glue lyophilizate and stored in frozen condition as a stable fibrinogen/F XIII preparation. This is a further advantage of the formulations in accordance with the invention because refreezing is not possible with the commercial frozen or lyophilized protein preparations that are used as tissue adhesives. This property simplifies the handling of lyophilizates after the reconstitution, or of frozen stored preparations if the entire quantity is not used in one process.

The following examples explain the production of fibrinogen-, fibrinogen/Factor XIII- or Factor XIII-concentrates to examine the stability of various formulations. It is also possible, for example, to use fibrinogen, F XIII or thrombin from transgenic or recombinant production as starter materials:

EXAMPLE 1

A fibrinogen concentrate was prepared from cryoprecipitate through precipitation, Al(OH)$_3$-adsorption, virus inactivation, and further precipitation (see P. Fuhge, P. Gratz, H. Geiger. "Moderne Methoden für die Herstellung von Gerinnungstherapeutika. (Modern methods for the preparation of coagulation therapeutics). Behring Inst. Mitt. 79:164–176 (1986)). Various chemical or physical processes can be used to inactivate or remove a virus. Said processes are effective for coated or non-coated viruses. The fibrinogen concentrate was adjusted to the respective composition as well as to a final fibrinogen concentration of more than 15 mg/ml, preferably more than 60 mg/ml, with diafiltration and subsequent concentration. The stability of these fibrinogen preparations was determined in the presence of 0.05% sodium azide and stored at the respective temperature and testing of the relevant analysis parameters such as coagulatable fibrinogen, F XIII-activity, viscosity, protein breakdown through SDS-PAGE, etc.

EXAMPLE 2

Purified Factor XIII was prepared from a plasma fraction containing F XIII (Cohn-Fraction I) (H. E. Karges and R. Rapp: Production and virus safety of human F XIII concentrates. In: Factor XIII, eds. J. McDonagh, R. Seitz, R. Egbring, Schattauer, Stuttgart/New York, pp. 66–76 (1993)). After dialysis or diafiltration and, if necessary, ultra filtration, this F XIII-solution was mixed with the stabilizers to be tested and stored at various temperatures after sterile filtration, or used as standard addition for fibrinogen concentrates.

EXAMPLE 3

As in Example 1, a fibrinogen concentration was prepared and the F XIII-content was topped off by adding a Factor XIII-solution. The preparations used for the stability analysis were prepared by subsequent dialysis and concentration to approximately 60 mg/ml fibrinogen and higher as well as 10 E/ml Factor XIII and higher. To prevent the growth of bacteria, the batches also contained 0.05% sodium azide or were filtered sterile with filters of 0.2 µm pore size.

EXAMPLE 4

The lyophilized fibrinogen concentrate of a commercial fibrin glue (Beriplast P) was reconstituted in water for injection purposes or in an aprotinin solution to a fibrinogen strength of >15 mg/ml, preferably to >60 mg/ml, and dialyzed against mixtures with various additives. In the presence of 0.05% NaN$_3$ to avoid the growth of bacteria, the fibrinogen/F XIII-concentrates were stored and their stability was analyzed at various times.

EXAMPLE 5

A fibrinogen concentrate was prepared from cryoprecipitate with subsequent AL(OH)$_3$-adsorption and inactivation of the virus, and the F XIII-concentration of said fibrinogen concentrate was topped off with the addition of purified F XIII, if necessary. This concentration was adjusted to the respective composition as well as to a final fibrinogen concentration of more than 15 mg/ml, preferably more than 40 mg/ml, by diafiltration and subsequent concentration. To test the storage stability, it was stored in the presence of 0.05% sodium azide.

EXAMPLE 6

Fibrinogen-/Factor XIII-concentrations were prepared according to the aforementioned examples and dialyzed and lyophilized against various formulation buffers. The resulting lyophilizates were tested directly for stability, or the solutions obtained after reconstitution were stored at temperatures of 0–10° Celsius and their stability was reviewed as indicated.

The stability of fibrinogen-, F XIII- as well as fibrinogen-F XIII-preparations prepared according to one of the examples 1–6 was determined by storage at the respective temperature and by testing the relevant analysis parameters. The results of these tests are listed in Tables 1 to 3. Generally, however, there are also other appropriate methods for the production of fibrinogen or Factor XIII, which can comprise other purification steps.

B) Concentrates stored in liquid state, containing Fibrinogen- or Fibrinogen/Factor XIII-concentrate (see Tables 1 and 2)

Even with liquid fibrinogen- or fibrinogen/Factor XIII-concentrates that are not frozen but are stored only in refrigerated state around 0 to 10° Celsius, the aggregation and thus the increase in viscosity must be controlled with the addition of chaotropic agents. This generally leads to a more or less severe drop in the activity of Factor XIII (compare Table 1, Batch 4 and 5). It has now been found that the increase in viscosity can be prevented or reduced and that the drop in Factor XIII can be decreased if the chaotropic substance is used in a quantity of less than 0.28 mol/liter. Arginine, guanidine, citruiline, nicotine amide and their mixtures have proven to be suitable chaotropic substances if they are employed in the aforementioned quantity. It is furthermore advantageous to add an anti-fibrinolytic such as aprotinin, lysine, ε-amino caproic acid (EACA), p-aminomethylbenzoic acid (PAMBA) or one of their physiologically safe salts or derivatives to the preparation, as well as physiologically safe salts of organic carboxylic acids, especially citric acid or lactic acid and, if necessary, one or more amino acids or a mono- or disaccharide or sugar alcohol as a further stabilizer of the fibrinogen- or fibrinogen-/Factor XIII-preparation. In this way, it is possible to obtain improved stabilities in fibrinogen concentrates with a fibrinogen strength of more than 15 mg/ml, especially of more than 60 mg/ml, when using chaotropic agents in a quantity of up to 0.28 M.

If mixtures of fibrinogen and Factor XIII are prepared, the simultaneous presence of chaotropic agents and the aforementioned additives or mixtures guarantee that the preparations reach improved stability values for fibrinogen as well as for F XIII in comparison to the known formulations. This mixture of fibrinogen and F XIII can be provided in combination with a preparation that contains thrombin to be used together as tissue adhesive in one packaging unit designed for this purpose.

C) Liquid concentrates with separate storage of fibrinogen and F XIII (see Tables 1–3)

It was shown that the stability of a liquid preparation comprising fibrinogen and F XIII could be further improved if fibrinogen and Factor XIII were stored separately and were not mixed together until immediately prior to or during the application. In that case, the F XIII-concentrate is stabilized independently of the fibrinogen. It has been shown that the Factor XIII preparation, which is essentially fibrinogen-free, can be stabilized with the addition of a physiologically safe salt of an organic di- or tri-carboxylic acid, especially citric acid, and the addition of further common stabilizers for F XIII in a quantity of up to 10 percent by weight, especially up to 5 percent by weight, as well as mixtures thereof, for storage in liquid state at 0 to 10° Celsius or 20 to 25° Celsius (see Table 3). Mono- or disaccharides or sugar alcohols and amino acids from the group of glycine, glycylglycine, alanine, cysteine, histidine, glutamine or physiologically safe salts of the glutamine acid or the asparagine acid or mixtures thereof are advantageously used as common stabilizers for F XIII. Furthermore, it is possible to add additives to control osmolarity, the pH-value, or other common stabilizers for F XIII, if necessary. The fibrinogen concentrate is stabilized as mentioned above.

The separate storage of Factor XIII- and fibrinogen preparations at 0 to 10° Celsius, which has respective specific stabilizers, allows the production of a fibrin glue that is comprised of three stable liquid components, i.e., the fibrinogen concentrate, F XIII-concentrate, and the thrombin concentrate. In this form, the components remain stable over a long time and retain their activity until they are mixed together immediately prior to or during the application as tissue glue. The formulations stated here also allow a freezing of the individual components without any significant loss of activity.

The F XIII and fibrinogen preparations stabilized in accordance with the invention can also be used parenterally or topically as independent components for therapeutic purposes.

Formulations Comprising Fibrinogen and/or F XIII
Formulations Analogous to the State of the Art 1. 0.1 mol/liter NaCl, 3 grams/liter $Na_3$-citrate×2 $H_2O$, 8 grams/liter glycine, 0.09 mol/liter L-arginine, 0.58 mol/liter AMCA, pH 7.4
2. 6 grams/liter $Na_3$-citrate×2 $H_2O$, 1% glycine, 2% nicotine amide, 1,000 KIE/ml aprotinin, pH 7.5
3. 1.8 grams/liter $Na_3$-citrate×2 $H_2O$, 16.3 grams/liter glycine, 0.36 grams/liter triton, 8.1 grams/liter HSA, 0.2 mol/liter nicotine amide, pH 7.3
4. 0.15 mol/liter NaCl, 0.29 mol/liter L-arginine, 1,000 KIE/ml aprotinin, pH 7.0
5. 0.15 mol/liter NaCl, 0.5 mol/liter urea, 1,000 KIE/ml aprotinin, pH 7.0

Formulations Made in Accordance with the Invention As Well As Comparative Batches Comprising Fibrinogen or Fibrinogen/Factor XIII 6. 6 grams/liter $Na_3$-citrate×2 $H_2O$, 0.12 mol/liter L-arginine, pH 7.4
7. 6 grams/liter $Na_3$-citrate×2 $H_2O$, 0.12 mol/liter L-arginine, 0.14 mol/liter citrulline, pH 7.4
8. 6 grams/liter $Na_3$-citrate×2 $H_2O$, 0.095 mol/liter L-arginine, 80 mmol/liter EACA, pH 7.4
9. 6 grams/liter $Na_3$-citrate×2 $H_2O$, 0.12 mol/liter L-arginine, 0.14 mmol/liter citrulline, 80 mmol/liter EACA, pH 7.4
10. 6 grams/liter $Na_3$-citrate×2 $H_2O$, 0.12 mol/liter L-arginine, 80 mmol/liter EACA, pH 7.4*
11. 0.1 mol/liter NaCl, 6 grams/liter $Na_3$.-citrate×2 $H_2O$, 0.24 mol/liter L-arginine, 80 mmol/liter EACA, pH 7.4
12. 0.1 mol/liter NaCl, 6 grams/liter $Na_3$.-citrate×2 $H_2O$, 0.24 mol/liter L-arginine, 320 mmol/liter L-lysine, pH 7.4
13. 6 mg/ml $Na_3$-citrate×2 $H_2O$, 0.12 mol/liter L-arginine, 0.14 mol/liter citrulline, 80 mmol/liter EACA, pH 7.4
14. 3 grams/liter $Na_3$-citrate×2 $H_2O$, 0.24 mol/liter L-arginine, 80 mmol/liter EACA, pH 7.0
15. 0.15 M NaCl, 6 grams/liter $Na_3$-citrate×2 $H_2O$, 0.24 mol/liter L-arginine, 1,000 KIE/ml aprotinin, pH 7.0
16. 6 grams/liter $Na_3$-citrate×2 $H_2O$, 0.24 mol/liter L-arginine×HCl, 80 mmol/liter EACA, pH 7.5
17. 6 grams/liter $Na_3$-citrate×2 $H_2O$, 0.24 mol/liter L-arginine×HCl, 80 mmol/liter PAMBA, pH 7.2
18. 6 grams/liter $Na_3$-citrate×2 $H_2O$, 0.24 mol/liter L-arginine×HCl, 8% mannitol, 80 mmol/liter EACA, pH 7.5
19. 6 grams/liter $Na_3$-citrate×2 $H_2O$, 0.15 M NaCl, 2% nicotine amide, 1,000 KIE/ml aprotinin, pH 7.5
20. 0.15 mol/liter NaCl, 6 grams/liter $Na_3$-citrate×2 $H_2O$, 0.24 mol/liter L-arginine, 320 mmol/liter lysine, pH 7.5
21. 0.15 mol/liter NaCl, 6 grams/liter $Na_3$.-citrate×2 $H_2O$ 0.24 mol/liter L-arginine, 80 mmol/liter EACA, pH 7.5
22. 6 grams/liter $Na_3$-citrate×2 $H_2O$, 0.24 mol/liter L-arginine, 320 mmol/liter lysine, pH 7.0
23. 6 grams/liter $Na_3$-citrate×2 $H_2O$, 0.24 mol/liter L-arginine, 80 mmol/liter EACA, pH 7.0
24. 0.15 mol/liter NaCl, 6 grams/liter $Na_3$-citrate×2 $H_2O$, 0.24 mol/liter L-arginine, 2% L-histidine, 1,000 KIE/ml aprotinin, pH 7.5
25. 0.15 mol/liter NaCl, 6 grams/liter $Na_3$-citrate×2 $H_2O$, 0.24 mol/liter L-arginine, 2% sucrose, 1,000 KIE/ml aprotinin, pH 7.5

Formulations Made in Accordance with the Invention, Comprising F XIII as Independent Component 26. 1.5 grams/liter $Na_3$-citrate×2 $H_2O$, 2.9 grams/liter NaCl, 3 grams/liter L-arginine×HCl, pH 7.4
27. 6 grams/liter $Na_3$-citrate×2 $H_2O$, pH 7.4
28. 1.5 grams/liter $Na_3$-citrate×2 $H_2O$, 2.9 grams/liter NaCl, pH 7.4
29. 3 grams/liter $Na_3$-citrate×2 $H_2O$, 1% glycine, pH 7.4
30. 3 grams/liter $Na_3$-citrate×2 $H_2O$, 2% mannitol, 10 mmol/liter L-histidine, pH 7.4
31. 6 grams/liter $Na_3$-citrate×2 $H_2O$, 2% mannitol, pH 7.4
32. 6 grams/liter $Na_3$-citrate×2 $H_2O$, 1% HSA, pH 7.4
33. 5 mmol/liter EDTA, 50 mmol/liter trismethylamine×HCl, pH 7.4
34. 6 grams/liter $Na_3$-citrate×2 $H_2O$, 1% L-histidine, pH 7.4
35. 1.5 grams/liter $Na_3$-citrate×2 $H_2O$, 2.92 grams/liter NaCl, 50 mmol/liter glycylglycine, pH 7.4
36. 3 grams/liter $Na_3$-citrate×2 $H_2O$, 1% L-histidine, pH 7.4
37. 3 grams/liter $Na_3$-citrate×2 $H_2O$, 38 mmol/liter glycylglycine, pH 7.4

* Batch prepared by reconstituting the appropriate lyophilizate with water for injection purposes TABLE 1a Stability of fibrinogen or fibrinogen/F XIII in various formulations at 4° Celsius

| Storage time | Batch | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Evaluation of viscosity (storage temperature: 4° Celsius): 1 = low viscosity, 2 = medium viscosity, 3 = high viscosity, 4 = solid at 4° Celsius. In all of the following tables, the storage time is stated in months: | | | | | | | | | | | | | |
| 0 | 1 | 1 | 1 | 1 | 1 | 1 | 1 | 1 | 1 | 1 | 1 | 1 | 1 |
| 0.5 | 1 | 1 | nd | 1 | 1 | 1 | 1 | 1 | 1 | nd | 1 | 1 | 1 |
| 1 | 1 | 2 | 2 | 1 | 1 | 1 | 1 | 1 | 1 | 1 | 1 | 1 | 1 |
| 3 | 2 | 3 | 3 | 1 | 1 | 1 | 1 | 1 | 1 | 1 | 1 | 1 | 1 |
| 6 | 2 | 4 | 3 | 1 | 1 | 1 | 1 | | 1 | 1 | 1 | 1 | 1 |
| 9 | 3 | nd | 3 | 1 | 1 | 1 | 1 | | 1 | | | | 1 |
| 12 | 3 | nd | | 1 | 1 | 1 | 1 | | 1 | | | | 1 |
| Fibrinogen (% of zero value), storage temperature: 4° Celsius | | | | | | | | | | | | | |
| 0 | 100 | 100 | 100 | 100 | 100 | 100 | 100 | 100 | 100 | 100 | 100 | 100 | 100 |
| 0.5 | 103 | 98 | Nd | 106 | 100 | 7 | 94 | 105 | 91 | nd | 104 | 95 | 91 |
| 1 | 99 | 94 | 98 | 110 | 97 | 92 | 91 | 109 | 95 | 102 | 109 | 103 | 95 |
| 3 | 99 | (96) | (100) | 111 | 98 | 89 | 92 | 104 | 91 | 103 | 108 | 99 | 91 |
| 6 | 100 | (100) | (90) | 97 | 89 | 92 | 87 | | 91 | 87 | 94 | 100 | 91 |
| 9 | (96) | Nd | (81) | 98 | 84 | 80 | 80 | | 86 | | | | 86 |
| 12 | (103) | nd | | 93 | 89 | 80 | 75 | | 90 | | | | 90 |
| Factor XIII (% of zero value); storage temperature: 4° Celsius | | | | | | | | | | | | | |
| 0 | 100 | 100 | 100 | 100 | 100 | 100 | 100 | 100 | 100 | 100 | | | 100 |
| 0.5 | 101 | 93 | nd | 73 | 81 | 98 | 100 | 100 | 102 | nd | | | 102 |
| 1 | 105 | 87 | 97 | 73 | 81 | 100 | 97 | 97 | 100 | 93 | | | 100 |
| 3 | 100 | (80) | (89) | 63 | 77 | 95 | 93 | 100 | 95 | 93 | | | 95 |
| 6 | 89 | (83) | (80) | 49 | 67 | 102 | 95 | | 95 | 83 | | | 95 |
| 9 | (98) | nd | (78) | 42 | 65 | 92 | 80 | | 86 | | | | 86 |
| 12 | (89) | nd | | 39 | 69 | 83 | 92 | | 85 | | | | 85 |

TABLE 1b

Stability of fibrinogen or fibrinogen/F XIII in various formulations at −20° Celsius

| Storage time | Batch | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Evaluation of viscosity after defrosting (storage temperatures: −20° Celsius); 1 = low viscosity, 2 = medium viscosity, 3 = high viscosity, 4 = solid at 4° Celsius | | | | | | | | | | | | | |
| 0 | 1 | 1 | 1 | nd | nd | 1 | 1 | 1 | 1 | nd | nd | nd | 1 |
| 0.5 | 1 | 1 | nd | nd | nd | nd | 1 | 1 | 1 | nd | nd | nd | 1 |
| 1 | 1 | 1 | 1 | nd | nd | 1 | 1 | 1 | 1 | nd | nd | nd | 1 |
| 3 | 1 | 1 | 1 | nd | nd | 1 | 1 | 1 | 1 | nd | nd | nd | 1 |
| 6 | 1 | 1 | 1 | nd | nd | 1 | 1 | 1 | 1 | nd | nd | nd | 1 |
| 9 | 1 | 1 | 1 | nd | nd | 1 | 1 | 1 | 1 | | | | 1 |
| 12 | 1 | 1 | | nd | nd | 1 | 1 | 1 | 1 | | | | 1 |
| Fibrinogen (% of zero value); storage temperature: −20 Celsius | | | | | | | | | | | | | |
| 0 | 100 | 100 | 100 | nd | nd | 100 | 100 | 100 | 100 | nd | nd | nd | 100 |
| 0.5 | 96 | 101 | nd | nd | nd | nd | 99 | 100 | 99 | nd | nd | nd | 99 |
| 1 | 100 | 95 | 95 | nd | nd | 99 | 100 | 101 | 93 | nd | nd | nd | 93 |
| 3 | 99 | 100 | 100 | nd | nd | 99 | 103 | 114 | 101 | nd | nd | nd | 101 |
| 6 | 99 | 101 | 105 | nd | nd | 100 | 106 | 115 | 103 | nd | nd | nd | 103 |
| 9 | 89 | nd | 108 | nd | nd | 93 | 104 | 100 | 94 | | | | 94 |
| 12 | 87 | nd | | nd | nd | 100 | 95 | 100 | 99 | | | | 99 |
| Factor XIII (% of zero value); storage temperature: −20°Celsius | | | | | | | | | | | | | |
| 0 | 100 | 100 | 100 | nd | nd | 100 | 100 | 100 | 100 | nd | nd | nd | 100 |
| 0.5 | 57 | 30 | nd | nd | nd | nd | 98 | 108 | 102 | nd | nd | nd | 102 |
| 1 | 48 | 8 | 15 | nd | nd | 100 | 102 | 102 | 95 | nd | nd | nd | 95 |
| 3 | 35 | 5 | 10 | nd | nd | 98 | 94 | 107 | 98 | nd | nd | nd | 98 |
| 6 | 24 | 5 | 15 | nd | nd | 107 | 98 | 102 | 97 | nd | nd | nd | 97 |
| 9 | 14 | nd | 10 | nd | nd | 95 | 100 | 102 | 93 | | | | 93 |
| 12 | 1 | nd | | nd | nd | 97 | 95 | 108 | 98 | | | | 98 |

TABLE 2a

Stability of fibrinogen or fibrinogen/F XIII in various formulations at 4° Celsius

| Storage time | 14 | 15 | 16 | 17 | 18 | 19 | 20 | 21 | 22 | 23 | 24 | 25 |
|---|---|---|---|---|---|---|---|---|---|---|---|---|
| Evaluation of viscosity after defrosting (storage temperature 4° Celsius); 1 = low viscosity, 2 = medium viscosity, 3 = high viscosity, 4 = solid at 4° Celsius ||||||||||||| |
| 0 | 1 | 1 | 1 | 1 | 1 | 1 | 1 | 1 | 1 | 1 | 1 | 1 |
| 0.5 | 1 | 1 | 1 | 1 | 1 | 1 | 1 | 1 | 1 | 1 | 1 | 1 |
| 1 | 1 | 1 | 1 | 1 | 1 | 1 | 1 | 1 | 1 | 1 | 1 | 1 |
| 3 | 1 | 1 | 1 | 1 | 1 | 1 | 1 | 1 | 1 | 1 | 1 | 1 |
| 6 | 1 | 1 | 1 | 1 | 1 | 1 | 1 | 1 | 1 | 1 |  | 1 |
| 9 | 1 | 1 | 1 | 1 | 1 | 1 | 1 | 1 | 1 | 1 |  | 1 |
| 12 |  | 1 | 1 |  | 1 | 1 | 1 | 1 |  |  |  |  |
| Fibrinogen (% of zero value), storage temperature: 4° Celsius ||||||||||||| |
| 0 | 100 | 100 | 100 | 100 | 100 | 100 | 100 | 100 | 100 | 100 | 100 | 100 |
| 0.5 | 100 | 93 | 98 | Nd | 98 | 99 | 94 | 91 | 92 | 96 | 97 | 101 |
| 1 | 95 | 93 | 95 | 99 | 102 | 91 | 101 | 94 | 91 | 94 | 96 | 96 |
| 3 | 84 | 87 | 90 | 105 | 112 | 99 | 98 | 86 | 89 | 94 | 83 | 94 |
| 6 | 97 | 79 | 96 | 108 | 118 | 101 | 92 | 82 | 90 | 102 |  | 87 |
| 9 | 95 | 88 | 89 | 94 | 112 | 109 | 98 | 88 | 96 | 97 |  |  |
| 12 |  | 77 | 82 |  | 96 | 94 | 86 | 78 |  |  |  |  |
| Factor XIII (% of zero value), storage temperature: 4° Celsius ||||||||||||| |
| 0 |  |  |  | 100 | 100 |  |  |  |  |  | 100 | 100 |
| 0.5 |  |  |  | Nd | 93 |  |  |  |  |  | 96 | 93 |
| 1 |  |  |  | 100 | 83 |  |  |  |  |  | 84 | 86 |
| 3 |  |  |  | 82 | 80 |  |  |  |  |  | 71 | 76 |
| 6 |  |  |  | 91 | 77 |  |  |  |  |  |  | 67 |
| 9 |  |  |  | 91 | 80 |  |  |  |  |  |  |  |
| 12 |  |  |  |  | 77 |  |  |  |  |  |  |  |

TABLE 2b

Stability of fibrinogen or fibrinogen/F XIII in various formulations at −20° Celsius

| Storage time | 14 | 15 | 16 | 17 | 18 | 19 | 20 | 21 | 22 | 23 | 24 | 25 |
|---|---|---|---|---|---|---|---|---|---|---|---|---|
| Evaluation of viscosity after defrosting (storage temperature: 20° Celsius); 1 = low viscosity, 2 = medium viscosity, 3 = high viscosity, 4 = solid at 4° Celsius ||||||||||||| |
| 0 | nd | 1 | 1 | nd | 1 | 1 | 1 | 1 | nd | nd | 1 | 1 |
| 0.5 | nd | 1 | 1 | nd | 1 | 1 | 1 | 1 | nd | nd | 1 | 1 |
| 1 | nd | 1 | 1 | nd | 1 | 1 | 1 | 1 | nd | nd | 1 | 1 |
| 3 | nd | 1 | 1 | nd | 1 | 1 | 1 | 1 | nd | nd | 1 | 1 |
| 6 | nd | 1 | 1 | nd | 1 | 1 | 1 | 1 | nd | nd |  | 1 |
| 9 | nd | 1 | 1 | nd | 1 | 1 | 1 | 1 | nd | nd |  |  |
| 12 | nd | 1 | 1 | nd | 1 | 1 | 1 | 1 | nd | nd |  |  |
| Fibrinogen (% of zero value), storage temperature: −20° C. Celsius ||||||||||||| |
| 0 | nd | 100 | 100 | nd | 100 | 100 | 100 | 100 | nd | nd | 100 | 100 |
| 0.5 | nd | 96 | 100 | nd | 100 | 96 | 91 | 86 | nd | nd | 90 | 94 |
| 1 | nd | 94 | 99 | nd | 98 | 100 | 99 | 93 | nd | nd | 94 | 97 |
| 3 | nd | 85 | 94 | nd | 94 | 92 | 97 | 93 | nd | nd | 85 | 90 |
| 6 | nd | 85 | 98 | nd | 98 | 90 | 99 | 92 | nd | nd |  | 89 |
| 9 | nd | 86 | 95 | nd | 100 | 87 | 91 | 79 | nd | nd |  |  |
| 12 | nd | 84 | 93 | nd | 98 | 87 | 84 | 81 | nd | nd |  |  |

TABLE 3

Stability of Factor XIII in various formulations at 4° Celsius, 20 to 25° Celsius and −20° Celsius

| Storage time | \| | \| | \| | \| | \| | Batch | \| | \| | \| | \| | \| | \| |
|---|---|---|---|---|---|---|---|---|---|---|---|---|
| | 26 | 27 | 28 | 29 | 30 | 31 | 32 | 33 | 34 | 35 | 36 | 37 |
| Factor XII, (% of zero value), storage temperature: 4° Celsius | | | | | | | | | | | | |
| 0 | 100 | 100 | 100 | 100 | 100 | 100 | 100 | 100 | 100 | 100 | 100 | 100 |
| 0.5 | 90 | 94 | Nd | nd | Nd | nd | nd | Nd | Nd | nd | nd | Nd |
| 1 | 95 | 94 | 128 | 96 | 114 | 104 | 101 | 76 | 100 | 97 | 116 | 108 |
| 3 | 105 | 101 | 134 | 110 | 113 | 108 | 104 | 114 | 116 | 115 | 116 | 134 |
| 6 | 112 | 102 | 136 | 110 | 105 | 106 | 103 | 106 | 114 | 103 | 103 | 114 |
| 9 | 116 | 112 | 133 | 112 | | 113 | 106 | 118 | 118 | 113 | 97 | 115 |
| 12 | | | | | | | | | | 117 | | 134 |
| Factor XII (% of hundred), storage temperature: −20° Celsius | | | | | | | | | | | | |
| 0 | | | 100 | | | | | | | | | |
| 0.5 | | | 92 | | | | | | | | | |
| 1 | | | 99 | | | | | | | | | |
| 3 | | | 97 | | | | | | | | | |
| 6 | | | 106 | | | | | | | | | |
| 9 | | | 108 | | | | | | | | | |
| 12 | | | 112 | | | | | | | | | |
| Factor XIII (% of zero value), storage temperature: 20 to 25° Celsius | | | | | | | | | | | | |
| 0 | | | | | | 100 | 100 | 100 | 100 | 100 | 100 | 100 |
| 0.5 | | | | | | nd | nd | nd | nd | nd | nd | nd |
| 1 | | | | | | 120 | 105 | 104 | 104 | 109 | 103 | 115 | 119 |
| 3 | | | | | | 111 | 112 | 105 | 113 | 112 | 109 | 108 | 120 |
| 6 | | | | | | 94 | 104 | 99 | 102 | 105 | 102 | 109 | 102 |
| 9 | | | | | | | 101 | 99 | 105 | 95 | 103 | 93 | 101 |
| 12 | | | | | | | | | | | 97 | | 105 |

What is claimed is:

1. A storage-quality tissue adhesive, comprising the following three separate components:
   a stabilized, essentially fibrinogen-free, protein preparation that is of storage quality in liquid state comprising blood coagulation Factor XIII;
   a stabilized protein preparation that is of storage-quality in liquid state comprising fibrinogen, and one or more chaotropic compounds; and
   a preparation containing thrombin;
   wherein the strength of the fibrinogen in the protein preparation containing fibrinogen is retained for at least two weeks when stored in the liquid state.

2. A storage-quality tissue adhesive, comprising two separate components:
   a stabilized protein preparation comprising:
      blood coagulation Factor XIII,
      fibrinogen, and
      one or more chaotropic compounds; and
   a preparation containing thrombin;
   wherein the strength of the fibrinogen in the protein preparation containing fibrinogen is retained for at least two weeks when stored in the liquid state.

3. A tissue adhesive in accordance with claims 1 or 2, wherein the protein preparation that contains Factor XIII further comprises one or more substances selected from stabilizers or buffer substances.

4. A tissue adhesive in accordance with claim 3, wherein the stabilizer is a physiologically safe salt of an organic di-, tri- or tetra carboxylic acid.

5. A tissue adhesive in accordance with claim 4, wherein the carboxylic acid is citric acid.

6. A tissue adhesive in accordance with claim 3, wherein the stabilizer is selected from a mono- or disaccharide or a sugar alcohol;
an amino acid selected from glycine, glycylglycine, alanine, cysteine, histidine, glutamine or a physiologically safe salt of glutamine- or asparagine acid;
an agent that reduces or prevents oxidation; or
a surface-active substance.

7. A tissue adhesive in accordance with claims 1 or 2, wherein the one or more chaotropic compounds is selected from arginine, guanidine, citrulline, urea or its derivatives or nicotine amide, and
   wherein the combined concentration of the chaotropic compounds is more than 0.04 mol/liter and less than 0.28 mol/liter.

8. A tissue adhesive in accordance with claims 1 or 2, wherein the protein preparation that contains fibrinogen further comprises one or more anti-fibrinolytic substances selected from aprotinin, ε-amino caproic acid (EACA), p-amino-methylbenzoic acid (PAMBA), lysine or one of their physiologically safe salts.

9. A tissue adhesive in accordance with claims 1 or 2, wherein the protein preparation that contains fibrinogen further comprises one or more substances selected from:
   a physiologically safe salt of an organic carboxylic acid,
   one or more amino acids,
   a mono- or disaccharide, or
   a sugar alcohol.

10. A tissue adhesive in accordance with claim 9, wherein the carboxylic acid is selected from citric acid or lactic acid.

11. A stabilized, frozen or lyophilized protein preparation comprising fibrinogen, Factor XIII and one or more chaotropic compounds, wherein the strength of the fibrinogen and Factor XIII in the preparation are retained at liquid storage for at least two weeks after defrosting or reconstitution, wherein the combined concentration of the chaotropic compounds is more than 0.04 mol/liters and less than 0.28 mol/liters, and wherein the content of inorganic salts is ≦100 mmol/liter.

12. A preparation in accordance with claim 11, wherein the content of inorganic salts is ≦50 mmol/liter.

13. A protein preparation in accordance with claim 11, wherein the one or more chaotropic compounds is selected from arginine, guanidine, urea or its derivatives thereof, or citrulline.

14. A protein preparation in accordance with claims 11 or 13, further comprising one or more anti-fibrinolytic substances selected from aprotinin, ε-amino caproic acid (EACA), p-aminomethylbenzoic acid (PAMBA), lysine, or one of their physiologically safe salts.

15. A protein preparation in accordance with claims 11 or 13, further comprising one or more substances selected from:
   a physiologically safe salt of an organic carboxylic acid,
   one or more amino acids,
   a mono- or disaccharide or
   a sugar alcohol.

16. A tissue adhesive in accordance with claim 15, wherein the carboxylic acid is selected from citric acid or lactic acid.

17. A protein preparation in accordance with claim 13, wherein the content of water-soluble inorganic salts of the preparation is ≦50 mmol/liter.

18. A protein preparation in accordance with claim 13, wherein the content of water-soluble inorganic salts of the preparation is ≦20 mmol/liter.

19. A protein preparation in accordance with claims 11 or 13, further comprising other plasma proteins, wherein the protein preparation can be used for the preparation of a tissue adhesive.

20. A method for connecting tissue comprising the parenteral or topical application of a preparation described in any one of claims 1, 2, 11 or 13.

* * * * *